United States Patent
Bischof et al.

(10) Patent No.: US 6,215,009 B1
(45) Date of Patent: Apr. 10, 2001

(54) MANUFACTURE OF CYCLOALKENYLPOLYENE ESTERS

(75) Inventors: Stefan Bischof, Riehen; David Carl Burdick, Binningen; Bernard Orsat, Allschwil, all of (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/484,905

(22) Filed: Jan. 18, 2000

(30) Foreign Application Priority Data

Feb. 22, 1999 (EP) .................................. 99103392

(51) Int. Cl.[7] .................................. C07C 51/00
(52) U.S. Cl. .......................... 554/127; 554/129; 554/154
(58) Field of Search .................................. 554/129, 127, 554/154

(56) References Cited

U.S. PATENT DOCUMENTS 2,577,538  12/1951  Milas et al. .
2,789,131   4/1957  Oroshnik et al. .

FOREIGN PATENT DOCUMENTS 629414  9/1949  (GB) .

OTHER PUBLICATIONS

Isler, et al., *Helv. Chim. Acta* XXXII, Fasc. II, No. 63, pp. 489–505 (1949).
Surmazis, et al., *J. Org. Chem.*, vol. 34, No. 10, pp. 3039–3041 (1969).
Schwieter, et al., *Helv Chim Acta* XLV, Fasc. II, No. 61–62, pp. 517–528 (1962).
Corey, et al., *J. Org. Chem.*, vol. 34, No. 11, pp. 3667–3668 (1969).
Wipf, et al., *Tetrahedron Letters*, vol. 38, No. 29, pp. 5073–5076 (1997).
Fristad, et al., *J. Org. Chem.*, vol. 45, pp. 3028–3037 (1980).
Dahmann, et al., *Liebigs Ann. Chem.*, pp. 837–845 (1994).
Caturla, et al., *Tetrahedron Letters*, vol. 37, No. 27, pp. 4787–4790 (1996).
Lythgoe, et al., *JACS*, pp. 4060–4065 (1956).

*Primary Examiner*—Deborah D. Carr
(74) *Attorney, Agent, or Firm*—Mark E. Waddell; Stephen M. Haracz; Bryan Cave LLP

(57) ABSTRACT

The invention provides a process for the manufacture of a retinyl acylate of the formula I:

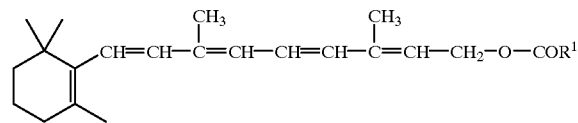

wherein $R^1$ is an optionally substituted $C_{1-23}$-alkyl, a $C_{2-23}$-alkenyl having 1 to 5 double bonds, an optionally aromatically substituted phenyl-$C_{1-6}$-alkyl, or an optionally substituted phenyl. This process includes treating a compound of formula II:

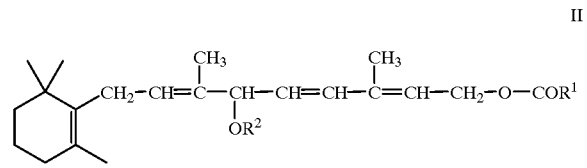

wherein $R^1$ is defined above and $R^2$ is hydrogen or $COR^1$, with an agent that is an acid anhydride or a complex of sulfur trioxide in the presence of dimethylformamide. In addition to dimethylformamide, an aprotic organic solvent may optionally be present in the reaction. The products of the present invention are useful as intermediates for the manufacture of compounds of the vitamin A group or in certain cases as the compounds themselves.

19 Claims, No Drawings

MANUFACTURE OF CYCLOALKENYLPOLYENE ESTERS

FIELD OF THE INVENTION

The present invention relates to a novel process for the manufacture of cycloalkenylpolyene esters, in particular retinyl acylates, which are 3,7-dimethyl-9-(2',6',6'-trimethylcyclohex-1'-en-1'-yl)-nona-2,4,6,8-tetraenyl acylates. Such compounds are of commercial interest as intermediates for the manufacture of compounds of the vitamin A group, or in certain cases as the compounds themselves.

The process involves an elimination and an isomerization of the corresponding 3,7-dimethyl-6-hydroxy-9-(2',6',6'-trimethylcyclohex-1'-en-1'-yl)-nona-2,4,7-trienyl acylate or of a 6-acylated derivative thereof using certain acid anhydrides or complexes thereof previously unknown as agents for this purpose.

SUMMARY OF THE INVENTION

The present invention provides a process for making a retinyl acylate of formula I:

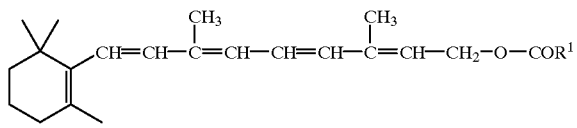

wherein $R^1$ is an optionally substituted $C_{1-23}$-alkyl, a $C_{2-23}$-alkenyl having 1 to 5 double bonds, an optionally aromatically substituted phenyl-$C_{1-6}$-alkyl, or an optionally substituted phenyl;

the process comprising reacting, in the presence of dimethylformamide, an agent which is an acid anhydride or a complex of sulfur trioxide with a compound of formula II:

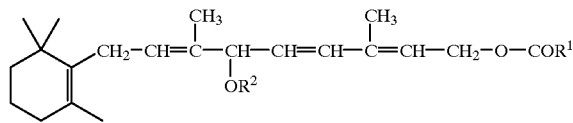

wherein $R^1$ is selected from the group consisting of an optionally substituted $C_{1-23}$-alkyl, a $C_{2-23}$-alkenyl having 1 to 5 double bonds, an optionally aromatically substituted phenyl-$C_{1-6}$-alkyl, and an optionally substituted phenyl; and $R^2$ is hydrogen or $COR^1$.

DETAILED DESCRIPTION OF THE INVENTION

Accordingly, the present invention provides a process for the manufacture of a retinyl acylate of formula I:

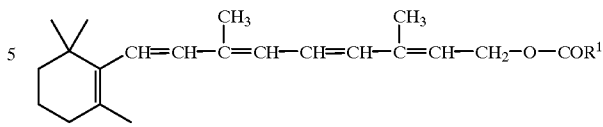

wherein $R^1$ is an optionally substituted $C_{1-23}$-alkyl; a $C_{2-23}$-alkenyl containing 1 to 5 double bonds; optionally aromatically substituted phenyl-$C_{1-6}$-alkyl; or an optionally substituted phenyl.

In this process, a compound of formula II:

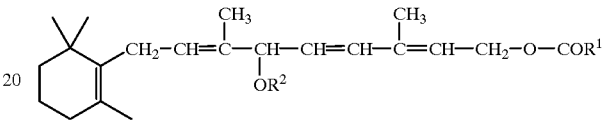

wherein $R^1$ is defined above and $R^2$ is hydrogen or $COR^1$, is treated with an agent which is an acid anhydride or a complex of sulfur trioxide. Such an agent is selected from trifluoroacetic anhydride; a $C_{1-6}$-alkanesulphonic acid anhydride; trifluoromethanesulphonic acid anhydride; an optionally substituted benzenesulphonic acid anhydride; phosphorus pentoxide; sulfur trioxide; and a complex of sulfur trioxide with a tri($C_{1-6}$-alkyl)amine, with a nitrogen-containing heteroaromatic compound or with a di($C_{1-6}$-alkyl)formamide. The treatment is effected in the presence of dimethylformamide which acts simultaneously as a solvent and a weak base.

As used herein, the term "$C_{1-23}$-alkyl" or "$C_{2-23}$-alkenyl containing (or having) 1 to 5 double bonds" with reference to $R^1$, depending on the number of carbon atoms, refers to not only straight-chain but also branched alkyl or alkenyl groups. Examples of $C_{1-23}$-alkyl groups include methyl, ethyl, propyl, pentyl, heptyl, undecyl, pentadecyl and heptadecyl. Examples of $C_{2-23}$-alkenyl groups include 8-heptadecenyl and heptadeca-8,11-dienyl. The corresponding alkanoyl and alkenoyl groups ($COR^1$) are acetyl, propionyl, butyryl, caproyl, capryl, dodecanoyl, palmitoyl and stearoyl and, respectively, oleoyl and linoleyl. Preferably, $R^1$ is methyl. In the case where $C_{1-23}$-alkyl is substituted, the substituents may be up to three $C_{1-4}$-alkoxy groups, which may, in each case, be straight-chain or branched. Two or three alkoxy substituents may be the same or different.

As used herein, the term "optionally aromatically substituted phenyl" means that the phenyl group is either unsubstituted or substituted with one or more substituents selected from for example alkyl, alkoxy and nitro groups and halogen atoms. These substituents may be up to three, and selected from 1 to 3 $C_{1-4}$-alkyl groups, 1 to 3 $C_{1-4}$-alkoxy groups, 1 to 2 nitro groups, and 1 to 3 halogen atoms. This applies equally to the "optionally substituted phenyl" group. Any alkyl or alkoxy substituent with 3 or 4 carbon atoms may be straight-chain or branched, and any halogen atom may be fluorine, chlorine, bromine or iodine.

The $C_{1-6}$-alkanesulphonic acid anhydride used in the process of the present invention for promoting the elimination and isomerization reaction involved, may be selected from methane-, ethane-, propane-, butane-, pentane- and hexanesulphonic acid anhydride, of which those featuring an alkane moiety with three to six carbon atoms can have a straight-chain or branched alkane moiety. If the "optionally substituted benzenesulphonic acid anhydride" is substituted, then the substituents may be, for example, one or more alkyl, alkoxy and nitro groups and halogen atoms, wherein each halogen atom may be fluorine, chlorine, bromine or iodine. The substituents may be up to three, and are selected from 1 to 3 $C_{1-4}$-alkyl groups, 1 to 3 $C_{1-4}$-alkoxy groups, 1 to 2 nitro groups, and 1 to 3 halogen atoms. The alkyl or alkoxy group with three or four carbon atoms may be straight-chain or branched.

In the case of a complex of sulfur trioxide with a tri($C_{1-6}$-alkyl)amine or a di($C_{1-6}$-alkyl)formamide, the alkyl groups may be straight-chain or branched, and the same or different. Examples of such alkyl groups include methyl, ethyl, n-propyl, isopropyl, n-butyl, isobutyl, tert.butyl, n-pentyl and n-hexyl. Examples of the trialkylamines include trimethylamine, triethylamine and N-ethyldiisopropylamine. An example of the dialkylformamides is dimethylformamide. In complexes of sulfur trioxide with a nitrogen-containing heteroaromatic compound, such compounds are especially heterocycles featuring at least one ring nitrogen atom. Pyridine and pyridine derivatives, such as picoline and quinoline, are examples. Such nitrogen-containing heteroaromatic compounds may also be bonded to a polymeric carrier ("polymer-bound"). Pyridine is the most preferred of these compounds. An example of a pyridine bonded to a polymeric carrier is poly-(4-vinyl-pyridine), the adduct of which with sulfur trioxide is commercially available.

The use of a complex of sulfur trioxide in the process of the present invention is advantageous by virtue of its simple production from the starting materials (educts) sulfur trioxide and the nitrogen containing compound. In addition, such an agent is easier to handle compared to the aggressive sulfur trioxide when used alone. The complexes are in part known and, in some cases, are commercially available. They may be produced readily by introducing sulfur trioxide into the diluted trialkylamine, nitrogen-containing heteroaromatic compound or dialkylformamide, methylene chloride, for example, being used as the diluent.

Preferred agents for use in the process of the present invention are phosphorus pentoxide, sulfur trioxide, and complexes of sulfur trioxide.

The process in accordance with the present invention is effected in the presence of dimethylformamide, which acts simultaneously as a solvent and as a weak base. However, an additional solvent may be present, which is generally an aprotic organic solvent. The solvent may be a polar or an apolar aprotic organic solvent and is suitably an aliphatic hydrocarbon with 5 to 10 carbon atoms, such as pentane, hexane, heptane or octane; an optionally alkyl-substituted alicyclic hydrocarbon with up to 10 carbon atoms, such as cyclohexane, methylcyclohexane or decalin; an aromatic hydrocarbon, such as benzene or toluene; a halogenated aliphatic hydrocarbon, such as methylene chloride, chloroform, carbon tetrachloride or dichloroethane; a nitrated aliphatic hydrocarbon, such as nitro-methane; an aliphatic ether, such as diethyl ether, diisopropyl ether, tert.butyl methyl ether or 1,2-dimethoxyethane; a cyclic ether, such as tetrahydrofuran, methylfuran or 1,4-dioxan; an aliphatic nitrile, such as acetonitrile; an aliphatic amine, such as triethylamine or N-ethyldiisopropylamine; an aliphatic or alicyclic amide (in addition to dimethylformamide itself), such as N,N-dimethylacetamide or 1-methyl-2-pyrrolidone, respectively; dimethyl sulphoxide; tetramethylene sulphone (sulfolane); or a mixture of one or more of the aforementioned solvents. Preferred additional solvents include aliphatic ethers, cyclic ethers, such as tetrahydrofuran, and dimethyl sulphoxide.

If a mixture of dimethylformamide with an aprotic organic solvent is used in the process of the present invention, the volume of the dimethylformamide in relation to the total volume of the solvent mixture is at least about 10% of the whole, and preferably at least about 20%. Preferred solvent mixtures are those containing dimethylformamide and, as the aprotic organic solvent, tetrahydrofuran or dimethyl sulphoxide.

The amount of agent used in accordance with the process of the present invention for promoting the elimination and isomerization reaction involved is from about 1 to about 3 molar equivalents per molar equivalent of starting material of formula II used. Preferably this amount is about 2 to about 3 molar equivalents.

The amount of dimethylformamide used in relation to the amount of starting material of formula II is about 1 to about 10 liters per mole.

The process of the present invention is carried out at temperatures from about −50° C. to about +50° C., preferably from about −35° C. to about +20° C.

The process of the present invention may be carried out by adding the agent which promotes the elimination and isomerization to the starting material of formula II in the dimethylformamide or solvent mixture containing dimethylformamide at the desired temperature. During the addition and the subsequent reaction, the reaction mixture may be stirred. Furthermore, the addition and subsequent reaction may be carried out under an inert gas atmosphere, such as under nitrogen or argon. Periodic checks of the progress of the reaction may be made using such known analytical techniques as reversed phase high pressure liquid chromatography (RP-HPLC) and normal phase HPLC (NP-HPLC). After completion of the reaction, which normally is achieved within about 20 hours, preferably within 10 hours, the mixture may be quenched with an organic base, such as a trialkylamine, preferably triethylamine, or a solid or aqueous inorganic base. If desired, the quenched mixture is held for several hours, and subsequently extracted, for example, with cold hexane, to isolate the product, which may then be purified, as necessary, using conventional methodology.

The starting material of formula II may be used in the process of the present invention as a single compound of formula II or as a mixture of two or more such compounds, both in respect of the isomeric form and in respect of the significance of $R^2$ (hydrogen or $COR^1$). For example, a mixture of a compound of formula II in which $R^2$ is hydrogen with one in which $R^2$ is $COR^1$, e.g. acetyl, may be used as the starting material.

In principle, the starting material of formula II may be in any isomeric form. In practice, the starting materials utilized feature various combinations of 2(Z)-, 4(Z)-, 7(Z)-, 2(E)-, 4(E)- and 7(E)-configured double bonds, as well as 6(S)- and 6(R)-configured carbon atoms (the 6-carbon atom bears the hydroxyl or acyloxy group $OR^2$). In view of the availability of the starting materials normally as mixtures of various isomeric forms or in particular isomeric forms, e.g. featuring 2(Z)-, 4(Z)- and 7(E)-configured double bonds, such mixtures or particular isomeric forms are generally employed.

The (all-E) isomers are more desirably used as the starting materials if readily available. However, an advantage of the process of the present invention resides in the result that whatever isomeric form of the starting material of formula II is used, the produced retinyl acylate of formula I features a high proportion of the most desirable (all-E) isomer. In this connection, it has been established that the temperature at which the process is performed exerts a significant influence on the selectivity in favor of the (all-E) isomer. In general, the lower the temperature, the higher the proportion of (all-E) isomer produced in any instance.

The following examples are provided to further illustrate the process of the present invention, whereby certain characteristics of the products are given. These examples are illustrative only and are not intended to limit the scope of the invention in any way.

EXAMPLES

Example 1

Synthesis of (all-E)-3,7-dimethyl-9-(2',6', 6'-trimethylcyclohex-1'-en-1'-yl)-nona-2,4,6,8-tetraenyl acetate ((all-E)-vitamin A acetate) from (2Z,4Z)-3,7-dimethyl-6-hydroxy-9-(2',6',6'-trimethylcyclohex-1'-en-1'-yl)-nona-2,4,6,8-tetraenyl acetate In a 100 ml round-bottomed flask equipped with a magnetic bar stirrer and flushed with argon were introduced 1020 mg (2.94 mmol) of (2Z,4Z)-3,7-dimethyl-6-hydroxy-9-(2',6',6'-trimethylcyclohex-1'-en-1'-yl)-nona-2,4,6,8-tetraenyl acetate and 30 ml of dimethylformamide. The stirred (350 rpm) homogeneous solution was cooled down to 0° C. (ice bath), and 1250 mg (8.82 mmol) of phosphorous pentoxide were rapidly added to the mixture. Then, the reaction mixture was stirred (350 rpm) at 0° C. (ice bath) for about 16 hours. After that reaction, the yield of (all-E)-vitamin A acetate was calculated on the basis of RP-HPLC to be 917.6 mg (94.9% yield based on the amount of starting material used; content: 83.8% all-E, 15.3% 2Z, 1.0% 2Z,4Z). The mixture was then quenched by adding rapidly 3.0 ml (21.52 mmol) of triethylamine at 0° C., stirred (350 rpm) at 0° C. for 15 minutes and then poured into approximately 70 ml of n-hexane and rapidly extracted. The layer separation was effected rapidly in order to keep the dimethylformamide phase cold during the extraction. This process was repeated six times with a total volume of approximately 450 ml of n-hexane. To ensure complete extraction, the remaining dimethylformamide phase was analyzed by RP-HPLC. The combined extracts were then concentrated in vacuo at 40–45° C. The residue (approximately 10 ml; n-hexane takes approximately 3% (v/v) dimethylformamide during extraction) still containing dimethylformamide was brought to 20 ml with dimethylformamide and the (all-E)-vitamin A acetate content was checked (calibrated RP-HPLC). The yield of (all-E)-vitamin A acetate was 880.2 mg (91.0% yield based on the amount of starting material used; content: 83.6% all-E, 15.4% 2Z, 1.0% 2Z,4Z). A UV determination at 325 nm in n-hexane confirmed this result. The dimethylformamide was then removed by evaporation in vacuo at 50° C. under light protection to yield 966.8 mg (99.9% w/w from starting material, 967.0 mg=100% w/w) of product as a yellow oil.

Example 2

Synthesis of (all-E)-3,7-dimethyl-9-(2',6',6'-trimethylcyclohex-1'-en-1'-yl 1)-nona-2,4,6,8-tetraenyl acetate ((all-E)-vitamin A acetate) from (2Z,4Z)-3,7-dimethyl-6-hydroxy-9-(2',6',6'-trimethylcyclohex-1'-en-1'-yl)-nona-2,4,6,8-tetraenyl acetate In a 100 ml round-bottomed flask equipped with a magnetic bar stirrer and flushed with argon were introduced 1020 mg (2.94 mmol) of (2Z,4Z)-3,7-dimethyl-6-hydroxy-9-(2',6',6'-trimethylcyclohex-1'-en-1'-yl)-nona-2,4,6,8-tetraenyl acetate and 30 ml of dimethylformamide. The stirred (350 rpm) homogeneous solution was cooled down to 0° C. (ice bath), and 900.0 mg (5.88 mmol) of 1:1-dimethylformamide-sulphur trioxide-complex were rapidly added to the mixture. Then, the reaction mixture was stirred (350 rpm) at 0° C. (ice bath) for about 20 hours. After that reaction, the yield of (all-E)-vitamin A acetate was calculated on the basis of RP-HPLC to be 926.0 mg (95.8% yield based on the amount of starting material used; content: 83.0% all-E, 15.7% 2Z, 1.2% 2Z,4Z). The mixture was then quenched by adding rapidly 2.0 ml (14.35 mmol) of cold triethylamine at 0° C., stirred (350 rpm) at 0° C. for 15 minutes and then poured into approximately 70 ml of n-hexane and rapidly extracted. The layer separation was effected rapidly in order to keep the dimethylformamide phase cold during the extraction. This process was repeated six times with a total volume of approximately 450 ml of n-hexane. To ensure complete extraction, the remaining dimethylformamide phase was analyzed by RP-HPLC. The combined extracts were then concentrated in vacuo at 40–45° C. The residue (approximately 10 ml; n-hexane takes approximately 3% (v/v) dimethylformamide during extraction) still containing dimethylformamide was brought to 20 ml with dimethylformamide and the (all-E)-vitamin A acetate content was checked (calibrated RP-HPLC). The yield of (all-E)-vitamin A acetate was calculated to be 907.5 mg (93.9% yield based on the amount of starting material used; content: 82.9% all-E, 15.9% 2Z, 1.3% 2Z,4Z). A UV determination at 325 nm in n-hexane confirmed this result. The dimethylformamide was then removed by evaporation in vacuo at 50° C. under light protection to yield 950.1 mg (93.3% wv/w from starting material, 967.0 mg=100% w/w) of product as a yellow oil.

Example 3

Synthesis of (all-E)-3,7-dimethyl-9-(2',6',6'-trimethylcyclohex-1'-en-1'-yl)-nona-2,4,6,8-tetraenyl acetate ((all-E)-vitamin A acetate) from (2Z,4Z)-3,7-dimethyl-6-hydroxy-9-(2',6',6'-trimethylcyclohex-1'-en-1'-yl)-nona-2,4,6,8-tetraenyl acetate In a 100 ml round-bottomed flask equipped with a magnetic bar stirrer and flushed with argon were introduced 1020 mg (2.94 mmol) of (2Z,4Z)-3,7-dimethyl-6-hydroxy-9-(2',6',6'-trimethylcyclohex-1'-en-1'-yl)-nona-2,4,6,8-tetraenyl acetate and 30 ml of dimethylformamide. The stirred (350 rpm) homogeneous solution was cooled down to 0° C. (ice bath), and 1920 mg (5.88 mmol) of p-toluenesulphonic acid anhydride were rapidly added to the mixture. Then, the reaction mixture was stirred (350 rpm) at 0° C. (ice bath) for about 16 hours. After that reaction, the yield of (all-E)-vitamin A acetate was calculated on the basis of RP-HPLC to be 909.4 mg (94.1% yield based on the amount of starting material used; content: 81.5% all-E, 17.2% 2Z, 1.3% 2Z,4Z). The mixture was then quenched by adding rapidly 2.0 ml (14.35 mmol) of triethylamine at 0° C., stirred (350 rpm) at 0° C. for 15 minutes and then poured into approximately 70 ml of n-hexane and rapidly extracted. The layer separation was effected rapidly in order to keep the dimethylformamide phase cold during the extraction. This process was repeated six times with a total volume of approximately 450 ml of n-hexane. To ensure complete extraction, the remaining dimethylformamide phase was analyzed by RP-HPLC. The combined extracts were then concentrated in vacuo at 40–45° C. The residue (approximately 10 ml;

n-hexane takes approximately 3% (v/v) dimethylformamide during extraction) still containing dimethylformamide was brought to 20 ml with dimethylformamide and the (all-E)-vitamin A acetate content was checked (calibrated RP-HPLC). The yield of (all-E)-vitamin A acetate was 898.7 mg (92.9% yield based on the amount of starting material used; content: 81.2% all-E, 17.5% 2Z, 1.4% 2Z,4Z). A UV determination at 325 nm in n-hexane confirmed this result. The dimethylformamide was then removed by evaporation in vacuo at 50° C. under light protection to yield 961.6 mg (99.4% w/w from starting material, 967.0 mg=100% w/w) of product as a yellow oil.

Example 4

Synthesis of (all-E)-3,7-dimethyl-9-(2',6',6'-trimethylcyclohex-1'-en-1'-yl)-nona-2,4,6,8-tetraenyl acetate ((all-E)-vitamin A acetate) from (2Z,4Z)-3, 7-dimethyl-6-hydroxy-9-(2',6',6'-trimethylcyclohex-1'-en-1'-yl)-nona-2,4,6,8-tetraenyl acetate In a 100 ml round-bottomed flask equipped with a magnetic bar stirrer and flushed with argon were introduced 1020 mg (2.94 mmol) of (2Z,4Z)-3,7-dimethyl-6-hydroxy-9-(2', 6',6'-trimethylcyclohex-1'-en-1'-yl)-nona-2,4,6,8-tetraenyl acetate and 30 ml of dimethylformamide. The stirred (350 rpm) homogeneous solution was cooled down to −45° C. to −50° C. (ice bath), and 534 μl (913.6 mg, 3.24 mmol) of trifluoromethanesulphonic acid anhydride were added to the mixture within 3–5 minutes. Then, the reaction mixture was stirred (350 rpm) at −45° C. to −50° C. for about 6 hours. After that reaction, the yield of (all-E)-vitamin A acetate was calculated on the basis of RP-HPLC to be 908.0 mg (93.9% yield based on the amount of starting material used; content: 88.3% all-E, 11.3% 2Z, 0.4% 2Z,4Z). The mixture was then quenched by adding rapidly 1 ml (7.17 mmol) of triethylamine at −45 to −50° C., well mixed and left to stir (350 rpm) at 0° C. for 20 minutes (until the internal temperature reached 0° C.) and then poured into approximately 70 ml of n-hexane and rapidly extracted. The layer separation was effected rapidly in order to keep the dimethylformamide phase cold during the extraction. This process was repeated six times with a total volume of approximately 450 ml of n-hexane. To ensure complete extraction, the remaining dimethylformamide phase was analyzed by RP-HPLC. The combined extracts were then concentrated in vacuo at 40–45° C. The residue (approximately 10 ml; n-hexane takes approximately 3% (v/v) dimethylformamide during extraction) still containing dimethylformamide was brought to 20 ml with dimethylformamide and the (all-E)-vitamin A acetate content was checked (calibrated RP-HPLC). The yield of (all-E)-vitamin A acetate was 840.8 mg (87.0% yield based on the amount of starting material used; content: 88.0% all-E, 11.5% 2Z, 0.5% 2Z,4Z). A UV determination at 325 nm in n-hexane confirmed this result. The dimethylformamide was then removed by evaporation in vacuo at 50° C. under light protection to yield 962.8 mg (99.6% w/w from starting material, 967.0 mg=100% w/w) of product as a yellow oil.

The invention being thus described, it will be obvious that the same may be varied in many ways. Such variations are not to be regarded as a departure from the spirit and scope of the invention and all such modifications are intended to be included within the scope of the following claims.

What is claimed is:
1. A process for making a retinyl acylate of formula I:

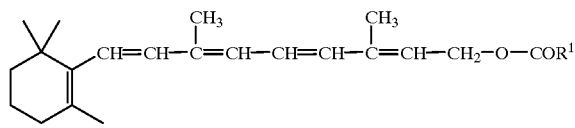

wherein
R$^1$ is an optionally substituted C$_{1-23}$-alkyl, a C$_{2-23}$-alkenyl having 1 to 5 double bonds, an optionally aromatically substituted phenyl-C$_{1-6}$-alkyl, or an optionally substituted phenyl;
the process comprising reacting, in the presence of dimethylformamide, an agent which is an acid anhydride or a complex of sulfur trioxide with a compound of formula II:

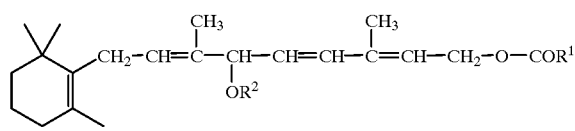

wherein
R$^1$ is selected from the group consisting of an optionally substituted C$_{1-23}$-alkyl, a C$_{2-23}$-alkenyl having 1 to 5 double bonds, an optionally aromatically substituted phenyl-C$_{1-6}$-alkyl, or an optionally substituted phenyl; and
R$^2$ is hydrogen or COR$^1$.
2. A process according to claim 1 wherein the agent is trifluoroacetic anhydride, C$_{1-6}$-alkanesulphonic acid anhydride, trifluoromethanesulphonic acid anhydride, an optionally substituted benzenesulphonic acid anhydride, phosphorus pentoxide, sulfur trioxide, or a complex of sulfur trioxide with a tri(C$_{1-6}$-alkyl)amine, with a nitrogen-containing heteroaromatic compound, or with di(C$_{1-6}$-alkyl) formamide.
3. A process according to claim 1 wherein R$^1$ is methyl.
4. A process according to claim 1 wherein the agent is phosphorus pentoxide, sulfur trioxide, or a complex of sulfur trioxide.
5. A process according to claim 3 wherein the agent is phosphorus pentoxide, sulfur trioxide, or a complex of sulfur trioxide.
6. A process according to claim 1 wherein an aprotic organic solvent is added to the reaction.
7. A process according to claim 3 further wherein an aprotic organic solvent is added to the reaction.
8. A process according to claim 4 further wherein an aprotic organic solvent is added to the reaction.
9. A process according to claim 6 wherein the aprotic organic solvent is selected from the group consisting of an aliphatic hydrocarbon with 5 to 10 carbon atoms, an optionally alkyl-substituted alicyclic hydrocarbon with up to 10 carbon atoms, an aromatic hydrocarbon, a halogenated aliphatic hydrocarbon, a nitrated aliphatic hydrocarbon, an aliphatic ether, a cyclic ether, an aliphatic nitrile, an aliphatic amine, an aliphatic or alicyclic amide, dimethyl sulphoxide, tetramethylene sulphone, and mixtures thereof.
10. A process according to claim 9 wherein the aprotic organic solvent is an aliphatic ether or a cyclic ether.

11. A process according to claim 10 wherein the aprotic organic solvent is tetrahydrofuran.

12. A process according to claim 10 wherein the aprotic organic solvent is dimethyl sulphoxide.

13. A process according to claim 6 wherein dimethylformamide is present in at least about 10% by volume compared to the total volume of the aprotic organic solvent and the dimethylformamide.

14. A process according to claim 6 wherein the dimethylformamide is present in at least 20% by volume compared to the total volume of the aprotic organic solvent and the dimethylformamide.

15. A process according to claim 1 wherein the agent is present in about 1 to about 3 molar equivalents per molar equivalent of the compound of formula II.

16. A process according to claim 15 wherein the agent is present in about 2 to about 3 molar equivalents per molar equivalent of the compound of formula II.

17. A process according to claim 1 wherein the amount of dimethylformamide used in relation to the amount of the compound of formula II is about 1 to about 10 liters per mole.

18. A process according to claim 1 wherein the compound of formula II is reacted with the agent at a temperature from about −50° C. to about +50° C.

19. A process according to claim 18 wherein the compound of formula II is reacted with the agent at a temperature from about −35° C. to about +20° C.

* * * * *

UNITED STATES PATENT AND TRADEMARK OFFICE
CERTIFICATE OF CORRECTION

PATENT NO. : 6,215,009 B1
DATED : April 10, 2001
INVENTOR(S) : Stefan Bischof, et al.

It is certified that error appears in the above-identified patent and that said Letters Patent is hereby corrected as shown below:

Title page,
Under [56] References Cited, OTHER PUBLICATIONS, in the second listed reference, please change "Surmazis" to -- Surmatis --.

Signed and Sealed this

Thirteenth Day of November, 2001

Attest:

*Nicholas P. Godici*

NICHOLAS P. GODICI
*Attesting Officer*    *Acting Director of the United States Patent and Trademark Office*